United States Patent
Bretschneider et al.

(10) Patent No.: US 6,576,771 B1
(45) Date of Patent: Jun. 10, 2003

(54) OXYMETHOXY-3-ARYL-PYRONE DERIVATIVES

(75) Inventors: Thomas Bretschneider, Lohmar (DE); Reiner Fischer, Monheim (DE); Folker Lieb, Leverkusen (DE); Hermann Hagemann, Leverkusen (DE); Michael Ruther, Monheim (DE); Jörg Stetter, Wuppertal (DE); Wolfram Andersch, Bergisch Gladbach (DE); Christoph Erdelen, Leichlingen (DE); Gerd Hänssler, Leverkusen (DE); Norbert Mencke, Leverkusen (DE); Klaus Stenzel, Düsseldorf (DE); Andreas Turberg, Haan (DE); Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/537,144

(22) Filed: Mar. 29, 2000

Related U.S. Application Data

(62) Division of application No. 09/077,237, filed as application No. PCT/EP96/05058 on Nov. 18, 1996, now Pat. No. 6,071,937.

(30) Foreign Application Priority Data

Nov. 29, 1995 (DE) .......................................... 195 44 457

(51) Int. Cl.$^7$ .............................. C07F 9/40; C07F 9/38; C07D 309/30
(52) U.S. Cl. ........................................ 549/216; 549/292
(58) Field of Search ................................. 549/216, 292

(56) References Cited

U.S. PATENT DOCUMENTS 5,393,729 A   2/1995   Fischer et al.

FOREIGN PATENT DOCUMENTS

EP   588137   3/1994

*Primary Examiner*—Patricia L. Morris
(74) *Attorney, Agent, or Firm*—Norris McLaughlin & Marcus

(57) ABSTRACT

The invention relates to novel oxymethoxy-3-aryl-pyrone derivatives of the formula (I)

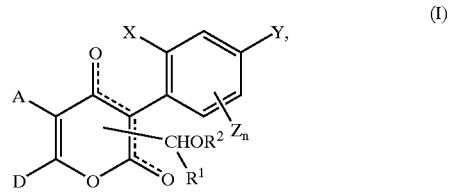

in which

A, D, $R^1$, $R^2$, X, Y, Z and n have the meanings specified in the description, a process for their preparation and their use as pesticides, fungicides and herbicides.

3 Claims, No Drawings

OXYMETHOXY-3-ARYL-PYRONE DERIVATIVES

This application is a divisional of application Ser. No. 09/077,237, filed on May 22, 1998 (now U.S. Pat No. 6,071,937, issued Jun. 6, 2000 which is a 371 PCT/EP96/05058 filed Nov. 18, 1996).

The invention relates to novel oxymethoxy-3-aryl-pyrone derivatives, a process for their preparation and their use as pesticides, fungicides and herbicides.

Certain phenyl-pyrone derivatives which are unsubstituted in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849 (1958)), no possible use as pesticides being specified for these compounds. Phenyl-ring-substituted phenyl-pyrone derivatives having herbicidal, acaricidal and insecticidal properties are described in EP-A-588 137.

However, the activity and spectrum of activity of these compounds is not always completely satisfactory, in particular at low application rates and concentrations. In addition, the tolerance by plants is frequently inadequate.

Novel compounds of the formula (I)

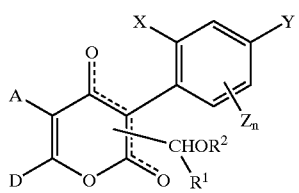

have now been found,
in which
- X represents halogen, nitro, cyano, alkyl, alkenyl, alkoxy, alkenyloxy, alkylthio, alkylsulfinyl, alkylsulfonyl, halogenoalkyl, halogenoalkenyl, halogenoalkoxy, halogenoalkenyloxy or in each case unsubstituted or substituted phenyl, phenoxy, phenylthio, benzyloxy or benzylthio,
- Y represents hydrogen, halogen, nitro, cyano, alkyl, alkenyl, alkoxy, alkenyloxy, alkylthio, alkylsulfinyl, alkylsulfonyl, halogenoalkyl, halogenoalkenyl, halogenoalkoxy or halogenoalkenyloxy,
- Z represents halogen, nitro, cyano, alkyl, alkenyl, alkoxy, alkenyloxy, halogenoalkyl, halogenoalkenyl, halogenoalkoxy or halogenoalkenyloxy,
- n represents one of the numbers 0, 1, 2 or 3,
- A represents hydrogen, halogen; an unsubstituted or substituted radical selected from the group comprising alkyl, cycloalkyl, alkenyl, alkinyl, arylalkyl, aryl, hetarylalkyl or hetaryl; or one of the groups —$COR^3$, —$CO_2R^3$, —CN, —$CONR^3R^4$, —$SO_2R^3$ or —$P(O)(OR^3)OR^4$, in which
  - $R^3$ and $R^4$ independently of one another represent hydrogen or in each case unsubstituted or substituted alkyl, alkenyl, arylalkyl, aryl, hetarylalkyl or hetaryl or
  - $R^3$ and $R^4$ together represent an unsubstituted or substituted alkylene group, in which one or more methylene groups is or are optionally replaced by the same number of hetero atoms,
- D represents hydrogen or an unsubstituted or substituted radical selected from the group comprising alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl and hetaryl or
- A and D together represent in each case an unsubstituted or substituted alkylene or alkenylene group, in each of which one or more methylene groups is or are optionally replaced by the same number of hetero atoms or hetero groups,
- $R^1$ represents hydrogen or alkyl which is optionally substituted by halogen and
- $R^2$ represents alkyl, alkenyl or alkinyl, each of which is optionally substituted by halogen.

The compounds of the formula (I) can also be present, depending on the nature of the substituents, as geometric and/or optical isomers or isomer mixtures, in differing composition, which can optionally be separated in a conventional manner. Both the pure isomers and the isomer mixtures, and their preparation and use and compositions containing these are subject-matter of the present invention.

However, for the sake of simplicity, compounds of the formula (I) will always be referred to below, although both the pure compounds and, optionally, also mixtures having differing proportions of isomeric compounds are intended.

The compounds of the formula (I) can, depending on the position of the keto group, occur in the two isomeric forms of the formulae $(I)_a$ and $(I)_b$,

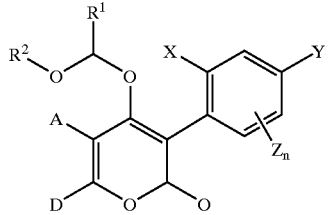

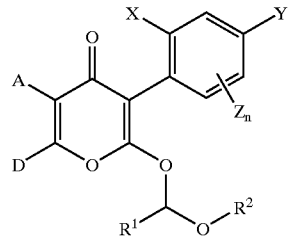

which is intended to be expressed by the dashed line in the formula (I).

The compounds of the formulae $(I)_a$ and $(I)_b$ can occur both as mixtures and in the form of their pure isomers. Mixtures of the compounds of the formulae $(I)_a$ and $(I)_b$ may optionally be separated by physical methods in a manner known per se, for example by chromatographic methods.

For reasons of increased clarity, only one of the possible isomers in each case will be cited below. This includes the possibility of the compounds, if appropriate, occurring in the form of the isomeric mixtures or in the other respective isomeric form.

It has further been found that the novel compounds of the formula (I)

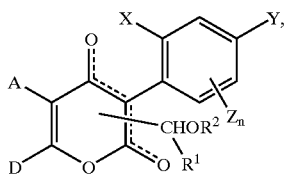

in which

A, D, X, Y, Z, $R^1$, $R^2$ and n have the meanings given above, are obtained when compounds of the formula (II)

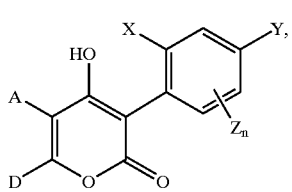

in which

A, D, X, Y, Z and n have the meanings given above, are reacted with compounds of the formula (III)

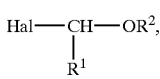

in which $R^1$ and $R^2$ have the meanings given above and

Hal represents halogen (preferably chlorine or bromine), in the presence or absence of a diluent and in the presence or absence of a reaction auxiliary.

It has further been found that the novel compounds of the formula (I), together with good tolerance by plants, have a very good activity as pesticides, preferably as insecticides and acaricides, but also against parasites in animal husbandry. Furthermore, some of the novel compounds of the formula (I) have very good microbicidal, preferably fungicidal, activity. Herbicidal activities were preferentially found at higher application rates.

The compounds according to the invention are generally defined by the formula (I). Preferred substituents or ranges of the radicals cited in the formulae mentioned above and below are described below:

X preferably represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulfinyl, $C_1$–$C_6$-alkylsulfonyl; $C_1$–$C_6$-alkyl, $C_2$–$C_6$-alkenyl, $C_1$–$C_6$-alkoxy or $C_2$–$C_6$-alkenyloxy, each of which is substituted by fluorine, chlorine or bromine; or phenyl, phenoxy, phenylthio, benzyloxy or benzylthio, each of which is optionally substituted by fluorine, chlorine, bromine, iodine, nitro, cyano or by $C_1$–$C_6$-alkyl or $C_1$–$C_6$-alkoxy, each of which is optionally substituted by fluorine, chlorine or bromine.

Y preferably represents hydrogen, fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulfinyl, $C_1$–$C_6$-alkylsulfonyl; or $C_1$–$C_6$-alkyl, $C_2$–$C_6$-alkenyl, $C_1$–$C_6$-alkoxy or $C_2$–$C_6$-alkenyloxy, each of which is substituted by fluorine, chlorine or bromine.

Z preferably represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy; or $C_1$–$C_6$-alkyl, $C_2$–$C_6$-alkenyl, $C_1$–$C_6$-alkoxy or $C_2$–$C_6$-alkenyloxy each of which is substituted by fluorine, chlorine or bromine.

n preferably represents one of the numbers 0, 1, 2 or 3.

A preferably represents hydrogen, fluorine, chlorine, bromine or iodine; a radical selected from the group consisting of $C_1$–$C_{10}$-alkyl, $C_3$–$C_{10}$-cycloalkyl, $C_3$–$C_{10}$-alkenyl and $C_3$–$C_{10}$-alkinyl, which radical is optionally substituted by fluorine, chlorine, bromine or iodine; a radical selected from the group consisting of phenyl, naphthyl, 5- or 6-membered hetaryl having one to three hetero atoms selected from the group consisting of oxygen, sulfur and nitrogen, phenyl-$C_1$–$C_6$-alkyl and 5- or 6-membered hetaryl-$C_1$–$C_6$-alkyl having one to three hetero atoms selected from the group consisting of oxygen, sulfur and nitrogen, which radical is optionally substituted by fluorine, chlorine, bromine, iodine, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or cyano, or one of the groups —$COR^3$, —$CO_2R^3$, —CN, —$CONR^3R^4$, —$SO_2R^3$ or —$P(O)(OR^3)OR^4$, in which $R^3$ and $R^4$ independently of one another represent hydrogen; $C_1$–$C_{10}$-alkyl or $C_3$–$C_{10}$-alkenyl, each of which is optionally substituted by fluorine, chlorine, bromine or iodine, or a radical selected from the group consisting of phenyl, naphthyl, 5- or 6-membered hetaryl having one to three hetero atoms selected from the group consisting of oxygen, sulfur and nitrogen, phenyl-$C_1$–$C_6$-alkyl and 5- or 6-membered hetaryl-$C_1$–$C_6$-alkyl having one to three hetero atoms selected from the group consisting of oxygen, sulfur and nitrogen, which radical is optionally substituted by fluorine, chlorine, bromine, iodine, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or cyano, or $R^3$ and $R^4$ together represent a $C_2$–$C_7$-alkylene group in which one non-terminal methylene group is optionally replaced by oxygen, sulfur, NH or N—$C_1$–$C_4$-alkyl.

D preferably represents hydrogen; $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by fluorine, chlorine, bromine or iodine; cyano-, $C_1$–$C_8$-alkyloxycarbonyl- or $C_1$–$C_8$-alkylcarbonyloxy-substituted $C_1$–$C_{12}$-alkyl; $C_3$–$C_8$-cycloalkyl, which is optionally substituted by halogen, $C_1$–$C_4$-alkyl, $C_1$–$C_4$-alkoxy or $C_1$–$C_4$-halogenoalkyl and in which one or two not directly adjacent methylene groups are optionally replaced by oxygen and/or sulfur; or phenyl, hetaryl having 5 to 6 ring atoms and one to three hetero atoms selected from the group consisting of oxygen, sulfur and nitrogen, phenyl-$C_1$–$C_6$-alkyl or hetaryl-$C_1$–$C_6$-alkyl having 5 to 6 ring atoms and one to three hetero atoms selected from the group consisting of oxygen, sulfur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together preferably represent a $C_2$–$C_7$-alkylene or $C_2$–$C_7$-alkenylene group, each of which is optionally substituted by $C_1$–$C_8$-alkyl, fluorine, chlorine, bromine or iodine and in which two carbon atoms are optionally joined by a $C_1$–$C_2$-alkylene group and in which a methylene group is optionally replaced by oxygen, sulfur, NH, N—$C_1$–$C_4$-alkyl or the group —O—CO—.

$R^1$ preferably represents hydrogen or $C_1$–$C_8$-alkyl, which is optionally substituted by fluorine, chlorine, bromine or iodine.

$R^2$ preferably represents $C_1$–$C_{10}$-alkyl, $C_3$–$C_{10}$-alkenyl or $C_3$–$C_{10}$-alkinyl, each of which is optionally substituted by fluorine, chlorine, bromine or iodine.

X particularly preferably represents fluorine, chlorine, bromine, nitro, cyano, $C_1$–$C_6$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulfinyl, $C_1$–$C_4$-alkylsulfonyl; $C_1$–$C_4$-alkyl, $C_2$–$C_4$-alkenyl, $C_1$–$C_4$-alkoxy or $C_2$–$C_4$-alkenyloxy, each of which is substituted by fluorine or chlorine; or phenyl, phenoxy, phenylthio, benzyloxy or benzylthio, each of which is optionally substituted by fluorine, chlorine, bromine, nitro or cyano or by $C_1$–$C_4$-alkyl or $C_1$–$C_4$-alkoxy, each of which is optionally substituted by fluorine or chlorine.

Y particularly preferably represents hydrogen, fluorine, chlorine, bromine, nitro, cyano, $C_1$–$C_6$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulfinyl, $C_1$–$C_4$-alkylsulfonyl; or $C_1$–$C_4$-alkyl or $C_1$–$C_4$-alkoxy, each of which is substituted by fluorine or chlorine.

Z particularly preferably represents fluorine, chlorine, bromine, nitro, cyano, $C_1$–$C_6$-alkyl, $C_1$–$C_4$-alkoxy, $C_2$–$C_4$-alkenyloxy; or $C_1$–$C_4$-alkyl or $C_1$–$C_4$-alkoxy, each of which is substituted by fluorine or chlorine.

n particularly preferably represents one of the numbers 0, 1 or 2.

A particularly preferably represents hydrogen, fluorine, chlorine or bromine; a radical selected from the group consisting of $C_1$–$C_8$-alkyl, $C_3$–$C_8$-cycloalkyl, $C_3$–$C_8$-alkenyl and $C_3$–$C_8$-alkinyl, which radical is optionally substituted by fluorine, chlorine or bromine; a radical selected from the group consisting of phenyl, naphthyl, furanyl, thienyl, pyridyl, phenyl-$C_1$–$C_4$-alkyl, furanyl-$C_1$–$C_4$-alkyl, thienyl-$C_1$–$C_4$-alkyl and pyridyl-$C_1$–$C_4$-alkyl, which radical is optionally substituted by fluorine, chlorine, bromine, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or cyano; or one of the groups —$COR^3$, —$CO_2R^3$, —CN, —$CONR^3R^4$, —$SO_2R^3$ or —$P(O)(OR^3)OR^4$, in which $R^3$ and $R^4$ independently of one another represent hydrogen; $C_1$–$C_8$-alkyl or $C_3$–$C_8$-alkenyl, each of which is optionally substituted by fluorine, chlorine or bromine; or a radical selected from the group consisting of phenyl, furanyl, thienyl, pyridyl, phenyl-$C_1$–$C_4$-alkyl, furanyl-$C_1$–$C_4$-alkyl, thienyl-$C_1$–$C_4$-alkyl and pyridyl-$C_1$–$C_4$-alkyl, which radical is optionally substituted by fluorine, chlorine, bromine, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or cyano or $R^3$ and $R^4$ together represent a $C_2$–$C_6$-alkylene group, in which a non-terminal methylene group is optionally replaced by oxygen, sulfur, NH or N—$C_1$–$C_4$-alkyl.

D particularly preferably represents hydrogen; $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine; $C_1$–$C_8$-alkyl which is substituted by cyano, $C_1$–$C_6$-alkoxycarbonyl or $C_1$–$C_6$-alkylcarbonyloxy; $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl, and in which one or two non-directly adjacent methylene groups are optionally replaced by oxygen and/or sulfur; or phenyl, furanyl, imidazolyl, pyridyl, thiazolyl, pyrazolyl, pyrimidyl, pyridazyl, pyrazinyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together particularly preferably represent a $C_2$–$C_6$-alkylene or $C_2$–$C_6$-alkenylene group, each of which is optionally substituted by $C_1$–$C_4$-alkyl, fluorine, chlorine or bromine, in which two carbon atoms are optionally connected by a $C_1$–$C_2$-alkylene group and in which a methylene group is optionally replaced by oxygen, sulfur, NH, N—$C_1$–$C_4$-alkyl or the group —O—CO—.

$R^1$ particularly preferably represents hydrogen or $C_1$–$C_4$-alkyl which is optionally substituted by fluorine, chlorine or bromine.

$R^2$ particularly preferably represents $C_1$–$C_8$-alkyl, $C_3$–$C_8$-alkenyl or $C_3$–$C_8$-alkinyl, each of which is optionally substituted by fluorine, chlorine or bromine.

X very particularly preferably represents fluorine, chlorine, bromine, nitro, cyano, methyl, ethyl, n- or i-propyl, n-, s-, i- or t-butyl, vinyl, allyl, methallyl, methoxy, ethoxy, n- or i-propoxy, allyloxy, methallyloxy, trifluoromethyl, difluoromethoxy, trifluoromethoxy, trifluoroethoxy, methylthio, methylsulfinyl or methylsulfonyl.

Y very particularly preferably represents hydrogen, fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy, trifluoroethoxy, methylthio, methylsulfinyl or methylsulfonyl.

Z very particularly preferably represents fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy or trifluoroethoxy.

n very particularly preferably represents either of the numbers 0 or 1.

A very particularly preferably represents hydrogen, fluorine, chlorine or bromine; a radical selected from the group consisting of $C_1$–$C_6$-alkyl, $C_3$–$C_6$-cycloalkyl, $C_3$–$C_6$-alkenyl and $C_3$–$C_6$-alkinyl, which radical is optionally substituted by fluorine or chlorine; phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro; or one of the groups —$COR^3$, —$CO_2R^3$, —CN, —$CONR^3R^4$, —$SO_2R^3$ or —$P(O)(OR^3)$—$OR^4$, in which $R^3$ and $R^4$ independently of one another represent hydrogen; $C_1$–$C_6$-alkyl or $C_3$–$C_6$-alkenyl, each of which is optionally substituted by fluorine or chlorine; or phenyl which is optionally substituted by fluorine, chlorine, bromine, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or cyano, or $R^3$ and $R^4$ together represent one of the groups
—(CH$_2$)$_3$—, —(CH$_2$)$_4$—, —(CH$_2$)$_5$—, —CH$_2$—CH(CH$_3$(CH$_2$)$_2$—, CH$_2$O—(CH$_2$)$_2$— and —CH$_2$S—(CH$_2$)$_2$—.

D very particularly preferably represents hydrogen; C$_1$–C$_8$-alkyl, C$_3$–C$_4$-alkenyl, C$_3$–C$_4$-alkinyl, C$_1$–C$_6$-alkoxy-C$_2$–C$_4$-alkyl, poly-C$_1$–C$_4$-alkoxy C$_2$–C$_4$-alkyl or C$_1$–C$_4$-alkylthio-C$_2$–C$_4$-alkyl, each of which is optionally substituted by fluorine or chlorine; or C$_3$–C$_6$-cycloalkyl which is optionally substituted by fluorine, chlorine, methyl or ethyl and in which one or two non-directly adjacent methylene groups are optionally replaced by oxygen and/or sulfur; or phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together very particularly preferable represent one of the groups —(CH$_2$)$_3$, —(CH$_2$)$_4$, —(CH$_2$)$_5$—, —CH$_2$—CH(C$_3$)(CH$_2$)$_2$—, —CH$_2$O—(CH$_2$)$_2$, —CH$_2$S—)CH$_2$)$_2$— or

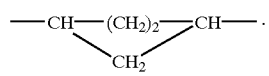

$R^1$ very particularly preferably represents hydrogen; or methyl or ethyl, each of which is optionally substituted by fluorine or chlorine.

$R^2$ very particularly preferably represents methyl, ethyl, n- or i-propyl, n-, i-, s- or t-butyl, allyl, methallyl, butenyl, propargyl or butinyl, each of which is optionally substituted by fluorine or chlorine.

The general radical definitions or explanations listed above or listed in preferred ranges can be combined in any manner among one another, that is to say including between the respective ranges and preferred ranges. They apply to the end products and also correspondingly to the precursors and intermediates.

According to the invention, preference is given to the compounds of the formula (I) which contain a combination of the meanings listed above as preferred.

According to the invention, particular preference is given to the compounds of the formula (I) which contain a combination of the meanings listed above as particularly preferred.

According to the invention, very particular preference is given to the compounds of the formula (I) which contain a combination of the meanings listed above as very particularly preferred.

Saturated or unsaturated hydrocarbon radicals such as alkyl or alkenyl can each be straight-chain or branched, as far as is possible, including in combination with hetero atoms, such as in alkoxy.

Radicals which may optionally be substituted can be monosubstituted or polysubstituted, where the substituents can be identical or different in the case of polysubstitution.

If, for example, 5-fluoro-3-[4-(2-bromo-4,6-dimethylphenyl)-4-hydroxy-6-methyl]-2-pyrone and propargyloxychloromethane are used as starting materials, the course of the process of the invention can be reproduced by the following reaction diagram:

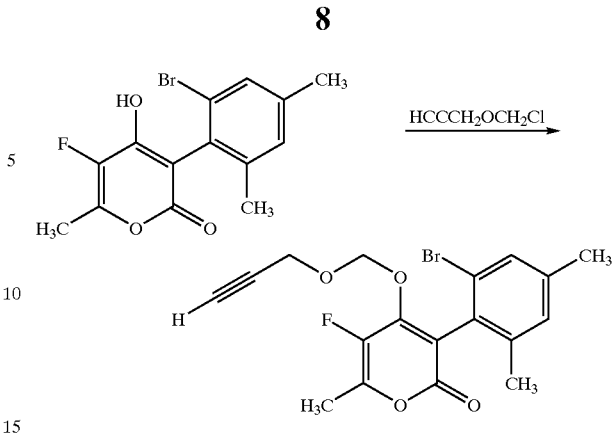

Some of the 4-hydroxy-2-pyrones of the formula (II) required as starting materials in the process of the invention are novel. They are described in EP-A-588 137 or are subject-matter of a prior, as yet unpublished, application by the applicant (German patent application having the file number 195 40 080.1 of 27.10.1995).

The compounds of the formula (III) required as starting materials in the process of the invention are compounds which are commercial, generally known or can be synthesized by known processes.

The process of the invention is characterized in that compounds of the formula (II) are reacted with α-alkoxy halides of the formula (III) in the presence or absence of a diluent and in the presence or absence of a reaction auxiliary.

Diluents which can be used in the process of the invention are all solvents which are inert to the halides. Those which can preferably be used are hydrocarbons, such as benzine, benzene, toluene, xylene and tetralin, in addition halogenated hydrocarbons, such as methylene chloride, chloroform, carbon tetrachloride, chlorobenzene and o-dichlorobenzene, in addition ketones, such as acetone and methyl isopropyl ketone, furthermore ethers, such as diethyl ether, tetrahydrofuran and dioxane, furthermore carboxylic esters, such as ethyl acetate, nitrites, such as acetonitrile, and also highly polar solvents, such as dimethylformamide, dimethyl sulfoxide and sulfolane. If the stability to hydrolysis of the halide permits, the reaction can also be carried out in the presence of water.

Reaction auxiliaries which are suitable in the reaction according to the process of the invention are, for example, all conventional acid acceptors. Those which can preferably be used are tertiary amines, such as triethylamine, pyridine, diazabicyclooctane (DABCO), diazabicycloundecene (DBU), diazabicyclononene (DBN), Hünig base and N,N-dimethylaniline, in addition alkaline earth metal oxides, such as magnesium oxide and calcium oxide, furthermore alkali metal carbonates and alkaline earth metal carbonates, such as sodium carbonate, potassium carbonate and calcium carbonate and alkali metal hydroxides such as sodium hydroxide and potassium hydroxide.

The reaction temperature can be varied within a relatively broad range in the process of the invention. Generally, temperatures between –20° C. and +150° C. are employed, preferably between 0° C. and 100° C.

When the process of the invention is carried out, the starting material of the formula (II) and the halide of the formula (III) are generally each used in approximately equivalent amounts. However, it is also possible to use the halide in a relatively great excess (up to 5 mol).

The reaction can be carried out at atmospheric pressure or under elevated pressure; atmospheric pressure is preferably employed. The work-up is performed by conventional methods of organic chemistry. The end products are preferably purified by crystallization, chromatographic purification or by so-called "incipient distillation", that is removal of the volatile constituents in vacuo.

The compounds according to the invention are suitable, with good crop tolerance and favorable toxicity to warm-blooded animals, for controlling animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.*

From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolietis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp, Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus,* Oscinella frit, Phorbia spp., *Pegomyla hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaricidal activity.

They can be employed particularly successfully to control insects which are harmful to plants, such as, for example, against the larvae of the mustard beetle (*Phaedon cochleariae*), against the caterpillars of the diamond-back moth (*Plutella maculipennis*), against the caterpillars of the owlet moth (*Spodoptera frugiperda*), against the larvae of the green rice leafhopper (*Nephotettix cincticeps*), against peach aphids (*Myzus persicae*) or against black bean aphids (*Aphis fabae*) and to control arachnids (Acari) which are harmful to plants, for example against the common spider mite (*Tetranychus urticae*).

The active compounds according to the invention have a high microbicidal activity and can be used in practice to control undesired microorganisms. The active compounds are also suitable for use as fungicides.

Fungicidal agents are employed in crop protection for controlling Plasmo-diophoromycetes, Oomycetes, Chytridiomycetes, Zygomycetes, Ascomycetes, Basidiomycetes and Deuteromycetes.

Bactericidal agents are employed in crop protection for controlling Pseudomonadaceae, Rhizobiaceae, Enterobacteriaceae, Corynebacteriaceae and Streptomycetaceae.

Non-limiting examples which may be mentioned of some pathogens causing fungal and bacterial diseases which come under the generic names listed above are:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea,*

Septoria species, such as, for example, *Septoria nodorum;*

Leptosphaeria species, such as, for example, *Leptosphaeria nodorum;*

Cercospora species, such as, for example, *Cercospora canescens,*

Alternaria species, such as, for example, *Alternaria brassicae;* and Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

In such treatments, the active compounds according to the invention are used particularly successfully for treating infestation by the fungus *Sphaerotheca fuliginea,* the causative organism of apple scab (*Venturia inaequalis*) and the fungi *Botrytis cinerea* and *Pyricularia oryzae* and, in addition, *Uncinula necator* and *Podosphaera leucotricha.*

The active compounds according to the invention can furthermore be used as defoliants, desiccants, haulm killers and, especially, as weedkillers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Arnaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotvledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotvledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are suitable for controlling monocotyledon and dicotyledon weeds in monocotyledon and dicotyledon crops, both in pre-emergence and in post-emergence treatments.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as extender, organic solvents, for example, can also be used as auxiliary solvents. The main liquid solvents which are suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulfoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or formers are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignin-sulfite waste liquors and methylcellulose.

Adhesives such as carboxymethylcellulose and natural and synthetic polymers in the form of powders, granules or latexes, such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, etc.

Particularly suitable mixing partners are, for example, the following:

Fungicides:

2-Aminobutane; 2-anilino-4-methyl-6-cyclopropyl-pyrimidine; 2',6'-dibromo-2-methyl-4'-trifluoromethoxy-4'-trifluoro-methyl- 1,3-thiazole-5-carboxanilide; 2,6-dichloro-N-(4-trifluoromethylbenzyl)benzamide, (E)-2-methoxyimino-N-methyl-2-(2-phenoxyphenyl)-acetamide; 8-hydroxyquinoline sulfate; methyl-(E)-2-{2-[6-(2-cyanophenoxy)-pyrimidin-4-yloxy]phenyl}-3-methoxyacrylate; methyl(E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, chinomethionat (quinomethionate), chloroneb, chloropicrin, chlorothalonil, chlozolinate, cufraneb, cymoxanil, cyproconazole, cyprofuram, dichlorophen, diclobutrazol, dichlofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides:

Bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/Acaricides/Nematicides:

Abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA-157 419, CGA 184699, cloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyraclofos, pyridaphenthion, pyresmethrin, pyrethrum, pyridaben, pyrimidifen, pyriproxyfen, quinalphos, RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; aryl-carboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzo-quat, dithiopyr, ethofumesate, fluorochloridone, glufosinate, glyphosate, isoxaben, pyridate, quinchlorac, quinmerac, sulfosate and tridiphane.

A mixture with fertilizers and growth regulators is also possible.

The active compound according to the invention can further be present in its commercially available formulations, and in the use forms prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. The active compounds according to the invention can be applied either before or after the emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

When used against hygiene pests and pests of stored products, the active compound is distinguished by an excellent residual action on wood and clay, as well as by a good stability to alkali on limed substrates.

The active compounds according to the invention are not only active against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the acaria (Acarida) and the orders of the metastigmata and mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (prostigmata) and Acaridida (astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

By way of example, they show an outstanding activity against Lucilia cuprina.

The active compounds of the formula (I) according to the invention are also suitable for controlling arthropods which infest agricultural productive livestock such as, for example, cattle, sheep, goats, horses, pigs, donkeys, camels, buffalos, rabbits, chickens, turkeys, ducks, geese and bees, other pets such as, for example, dogs, cats, cage birds and aquarium fish, and also so-called test animals such as, for example, hamsters, guinea pigs, rats and mice. By controlling these arthropods, cases of death and reductions in productivity (for meat, milk, wool, hides, eggs, honey etc.) should be diminished, so that simpler and more economic animal husbandry is made possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitoneal, etc.), implants, by nasal administration, by dermal use in the form, for example, of bathing or dipping, spraying, pouring on and spotting on, washing and powdering, and also with the aid of molded articles containing the active compounds, such as collars, ear tags, tail tags, limb bands, halters, marking devices, etc.

When used in connection with cattle, poultry, pets, etc., the active compounds of the formula (I) can be used as formulations (for example powders, emulsions, flowable compositions), which contain the active compound in an amount from 1 to 80% by weight, directly or after 100-fold to 10,000-fold dilution, or they can be used as a chemical bath.

Furthermore, it has been found that the compounds according to the invention of the formula (I) show high insecticidal action against insects which destroy industrial materials.

The following insects may be mentioned as examples and preferably, but not by way of limitation:

Beetles such as
  Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec. and Dinoderus minutus.
Hymenoptera such as
  Sirex juvencus, Urocerus gigas, Urocerus gigas taignus and Urocerus augur.
Termites such as
  Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis and Coptotermes formosanus.
Bristletails
  such as Lepisma saccharin.

Industrial materials in the present context are understood to be non-living materials, such as, preferably, plastics, glues, sizes, paper and board, leather, wood and wood-processing products and paints.

Very particularly preferably, the materials to be protected against insect infestation are wood and wood-processing products.

Wood and wood-processing products which can be protected by the composition according to the invention or mixtures containing it are understood to be, for example: construction timber, wooden beams, railroad sleepers, bridge components, landing-stages, wooden vehicles, crates, pallets, containers, telephone poles, wood cladding, wooden windows and doors, plywood, particle boards, joinery work or wooden products which are used quite generally in house building or joinery.

The active compounds can be used as such, in the form of concentrates or generally customary formulations such as powders, granules, solutions, suspensions, emulsions or pastes.

The said formulations can be produced in a manner known per se, for example by mixing the active compounds with at least one solvent or diluent, emulsifier, dispersant and/or binder or fixer, water-repellent, if appropriate driers and UV stabilizers and, if appropriate, dyestuffs and pigments and other processing aids.

The insecticidal compositions or concentrates used to protect wood and wooden materials contain the active compound according to the invention in a concentration of 0.0001 to 95% by weight, in particular 0.001 to 60% by weight.

The amount of the compositions or concentrates used depends on the type and incidence of the insects and on the medium. The optimum application rate can be determined by test series each time in use. However, it is generally sufficient to use 0.0001 to 20% by weight, preferably 0.001 to 10% by weight, of the active compound, based on the material to be protected.

As solvent and/or diluent, use is made of an organic chemical solvent or solvent mixture and/or an oily or oleaginous non-volatile organic chemical solvent or solvent mixture and/or a polar organic chemical solvent or solvent mixture and/or water and, if appropriate, an emulsifier and/or wetting agent.

As organic chemical solvents, use is preferably made of oily or oleaginous solvents having a relative evaporation rate greater than 35 and a flashpoint above 30° C., preferably above 45° C. As non-volatile, water-insoluble, oily and oleaginous solvents of this type, use is made of appropriate mineral oils or their aromatic fractions or mineral-oil-containing solvent mixtures, preferably white spirit, petroleum and/or alkylbenzene.

Those which are advantageously used are mineral oils having a boiling range from 170 to 220° C., white spirit having a boiling range from 170 to 220° C., spindle oil having a boiling range from 250 to 350° C., petroleum or aromatics of boiling range from 160 to 280° C., turpentine oil and the like.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthlene, preferably α-monochloronaphthlene, are used.

The organic non-volatile oily or oleaginous solvents having a relative evaporation rate greater than 35 and a flashpoint above 30° C., preferably above 45° C., can be replaced in part by readily or medium-volatile organic chemical solvents, with the proviso that the solvent mixture likewise has a relative evaporation rate greater than 35 and a flashpoint above 30° C., preferably above 45° C., and that the insecticide-fungicide mixture is soluble or emulsifiable in this solvent mixture.

According to a preferred embodiment, some of the organic-chemical solvent or solvent mixture is replaced by an aliphatic polar organic-chemical solvent or solvent mixture. Preferably, hydroxyl- and/or ester- and/or ether-group-containing aliphatic organic-chemical solvents such as, for example, glycol ethers, esters or the like are used.

As organic-chemical binders, in the context of the present invention, use is made of the binding drying oils and/or synthetic resins which are known per se and are water-dilutable and/or are soluble or dispersible or emulsifiable in the organic-chemical solvents used, in particular binders comprising or containing an acrylic resin, a vinyl resin, for example poly(vinyl acetate), polyester resin, polycondensation or polyaddition resin, polyurethane resin, alkyd resin or modified alkyd resin, phenolic resin, hydrocarbon resin such as indene-coumarone resin, silicone resin, drying vegetable oils and/or drying oils and/or physically drying binders based on a natural and/or synthetic resin.

The synthetic resin employed as binder can be used in the form of an emulsion, dispersion or solution. As binder, use can also be made of bitumen or bituminous substances up to 10% by weight. In addition, dyestuffs, pigments, water-repellent agents, reodorants and inhibitors or anti-corrosive agents and the like.

As organic-chemical binders, preference is given according to the invention to at least one alkyd resin or modified alkyd resin and/or a drying vegetable oil present in the composition or in the concentrate. Preferably, alkyd resins having an oil content of greater than 45% by weight, preferably 50 to 68% by weight, are used according to the invention.

The binder mentioned can be entirely or partially replaced by a fixing agent (mixture) or a plasticizer (mixture). These additions are intended to prevent volatilization of the active compounds or else a crystallization or precipitation. Preferably, they replace 0.01 to 30% of the binder (based on 100% of the binder used).

The plasticizers originate from the chemical classes of the phthalic esters, such as dibutyl, dioctyl or benzyl butyl phthalate, phosphoric esters, such as tributyl phosphate, adipic esters, such as di-(2-ethylhexyl) adipate, stearates, such as butyl stearate or amyl stearate, oleates, such as butyl oleate, glycerol ethers or higher-molecular glycol ethers, glycerol esters and p-toluenesulfonic esters.

Fixing agents are chemically based on poly(vinyl alkyl ethers) such as, for example, poly(vinyl methyl ether) or ketones, such as benzophenone and ethylene-benzophenone.

As solvent or diluent, water is also especially suitable, if appropriate in a mixture with one or more of the abovementioned organic-chemical solvents or diluents, emulsifiers and dispersants.

Particularly effective protection of wood is achieved by industrial impregnation processes, e.g. vacuum, double vacuum or pressure processes.

The ready-to-use compositions can, if appropriate, contain further insecticides and, if appropriate, one or more further fungicides.

Additional mixing partners which are suitable are preferably the insecticides and fungicides mentioned in WO 94/29 268. The compounds mentioned in this document are an explicit part of the present application.

Very particularly preferred mixing partners which may be mentioned are insecticides, such as chlorpyrifos, phoxim, silafluofen, alphamethrin, cyfluthrin, cypermethrin, deltamethrin, permethrin, imidacloprid, NI-25, flufenoxuron, hexaflumuron and triflumuron as well as fungicides such as epoxyconazole, hexaconazole, azaconazole, propiconazole, tebuconazole, cyproconazole, metconazole, imazalil, dichlofluanid, tolylfluanid, 3-iodo-2-propinyl-butyl carbamate, N-octyl-isothiazolin-3-one and 4,5-dichloro-N-octylisothiazolin-3-one.

The preparation and use of the active compounds according to the invention are given by the following examples.

PREPARATION EXAMPLES

Example 1

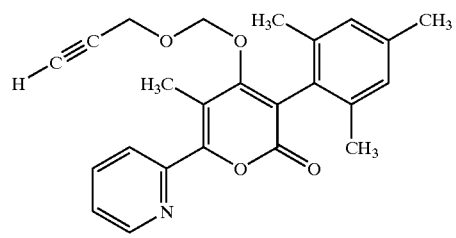

6.4 g (20 mmol) of 4-hydroxy-5-methyl-6-(2-pyridyl)-3-(2,4,6-trimethylphenyl)-2-pyrone in 50 ml of ethyl acetate are introduced in the absence of moisture. 2.02 g (20 mmol) of triethylamine are added thereto at 20° C. and a solution of 2.1 g (20 mmol) of propargyloxychloromethane in 20 ml of ethyl acetate is added dropwise at 0° C. with cooling. The mixture is further stirred for 20 h at 20° C. and the reaction is followed by thin-layer chromatography. The solution is filtered off from the precipitated triethylamine hydrochloride with suction and washed with ethyl acetate. The combined mother liquors are washed twice, each time with 50 ml of half-saturated common salt solution, dried over magnesium sulfate and evaporated in vacuo. 8 g of crude product are obtained. 6.4 g (82% of theory) of 5-methyl-6-(2-pyridyl)-4-propargyloxymethoxy-3-(2,4,6-trimethylphenyl)-2-pyrone are obtained as an oil by flash chromatography on 500 g of silica gel 60 (35–70 μm) using toluene:acetone 20:1 as mobile phase.

$^1$H-NMR (CDCl$_3$) δ[ppm]: 8.70 (m, 1H); 7.94 (td, 1H); 7.83 (m, 1H); 7.34 (m, 1H); 6.93 (s, 2H); 4.74 (s, 2H); 4.11 (d, 2H); 2.42 (t, 1H); 2.41 .(s, 3H); 2.30 (s, 3H); 2.20 (s, 6H).

Example 2

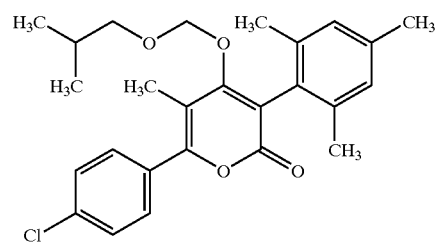

7.1 g (20 mmol) of 6-(4-chlorophenyl)-4-hydroxy-5-methyl-3-(2,4,6-trimethyl-phenyl)-2-pyrone in 50 ml of ethyl acetate are introduced in the absence of moisture. 2.02 g (20 mmol) of triethylamine are added thereto at 20° C. and a solution of 2.4 g (20 mmol) of i-butoxychloromethane in 20 ml of ethyl acetate is added dropwise at 0° C. with cooling. The mixture is then further stirred for 20 h at 20° C. and the reaction is followed by thin-layer chromatography. The solution is filtered off from the precipitated triethylamine hydrochloride using suction and washed with ethyl acetate. The combined mother liquors are washed twice, each time with 50 ml of half-saturated common salt solution, dried over magnesium sulfate and evaporated in vacuo. 8.8 g of crude product are obtained. 5.6 g (63% of theory) of 6-(4-chlorophenyl)-4-[(2-methyl-1-propoxy)-methoxy]-5-methyl-3-(2,4,6-trimethylphenyl)-2-pyrone are obtained as an oil by flash chromatography on 500 g of silica gel 60 (35–70 μm) using toluene:acetone 50:1 as mobile phase.

$^1$H-NMR (CDCl$_3$) δ[ppm]: 7.52 (AA'BB', 4H); 6.92 (s, 2H); 4.57 (s, 2H); 3.26 (d, 2H); 2.30 (s, 3H); 2.20 (s, 6H); 2.15 (s, 3H); 1.78 (m, 1H); 0.87 (d, 6H).

Examples 3–35

The compounds of the formula (I-a) which are listed in Table 1 below were obtained in a similar manner to Examples 1 and 2 and in accordance with the general details for preparation.

TABLE 1

(I-a)

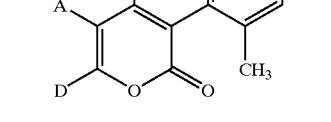

| Ex. No. | A | D | R$^1$ | R$^2$ | Physical data: m.p. or $^1$H-NMR (CDCl$_3$): δ [ppm] |
|---|---|---|---|---|---|
| 3 | H | CH$_3$ | H | CH$_2$CH$_3$ | 133–135° C. |
| 4 | CH$_3$ | 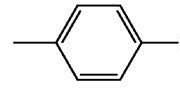 | H | CH$_2$CH$_3$ | 156–158° C. |
| 5 | H | CH$_2$CH(CH$_3$)$_2$ | H | CH$_2$CH$_3$ | 6.91(s 2H); 6.28(s 1H); 5.12(s 2H); 3.60 (q 2H); 2.42(d 2H); 2.28(s 3H); ~2.2(m 1H); 2.10(s 6H); 1.18(t 3H); 1.00(d 6H) |
| 6 | |  | H | CH$_2$CH$_3$ | 6.88(s 2H); 5.00(AB 2H); 3.63(bs 1H); 3.53 (q 2H); 3.25(bs 1H); 2.26(s 3H); 2.10(s 1H); 2.04(s 3H); 1.93 (m 2H); 1.81(m 1H); 1.25–1.45(m 3H); 1.14 (t 3H) |
| 7 | CH$_3$ | 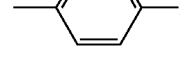 | H | CH$_2$C≡CH | 104–106° C. |
| 8 | CH$_3$ | 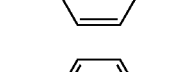 | H | CH$_2$CH(CH$_3$)$_2$ | 91–93° C. |
| 9 | CH$_3$ |  | H | CH(CH$_3$)$_2$ | 77–79° C. |
| 10 | CH$_3$ |  | H | CH$_2$CH(CH$_3$)$_2$ | 8.70(m 1H); 7.93(td 1H); 7.83(m 1H); 7.33 (m 1H); 6.91(s 2H); 4.58(s 2H); 3.26(d 2H); 2.40(s 3H); 2.28 (s 3H); 2.18(s 6H); 1.77(m, 1H); 0.86(d, 6H) |
| 11 | CH$_3$ |  | H | CH(CH$_3$)$_2$ | 83–85° C. |

TABLE 1-continued

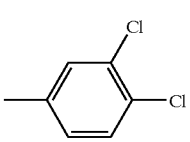

(I-a)

| Ex. No. | A | D | R¹ | R² | Physical data: m.p. or ¹H-NMR (CDCl₃): δ [ppm] |
|---|---|---|---|---|---|
| 12 | H | 3,4-dichlorophenyl | H | CH₂C≡CH | 143–145° C. |
| 13 | H | 3,4-dichlorophenyl | H | CH₂CH(CH₃)₂ | 128–131° C. |
| 14 | H | 3,4-dichlorophenyl | H | CH(CH₃)₂ | 140–142° C. |
| 15 | | —(CH₂)₄— | H | CH₂C≡CH | 123–125° C. |
| 16 | | —(CH₂)₄— | H | CH₂CH(CH₃)₂ | 67–69° C. |
| 17 | CH₃ | 4-chlorophenyl | H | CH₂C≡CH | 108–110° C. |
| 18 | CH₃ | 4-chlorophenyl | H | CH(CH₃)₂ | 101–103° C. |
| 19 | H | 1-chlorocyclopropyl | H | CH₂C≡CH | 6.92(s 2H); 6.85(s 1H); 5.26(s 2H); 4.20 (d 2H); 2.43(t 1H); 2.30(s 3H); 2.09(s 6H); 1.83(AA′ 2H); 1.51(BB′ 2H) |
| 20 | H | 1-chlorocyclopropyl | H | CH₂CH(CH₃)₂ | 94–97° C. |
| 21 | H | 1-chlorocyclopropyl | H | CH(CH₃)₂ | 6.93(s 1H); 6.91(s 2H); 5.19(s 2H); 3.85 (sp 1H); 2.28(s 3H); 2.08(s 6H); 1.84(AA′ 2H); 1.51(BB′ 2H); 1.14(d 6H) |
| 22 | CH₃ | 2-furyl | H | CH₂CH(CH₃)₂ | 7.58(d 1H); 7.05(d 1H); 6.91(s 2H); 6.57 (dd 1H); 4.53(s 2H); 3.23(d 2H); 2.23(s 3H); 2.28(s 3H); 2.17 (s 6H); 1.76(m 1H); 0.87(d 6H) |

TABLE 1-continued (I-a)

| Ex. No. | A | D | R¹ | R² | Physical data: m.p. or ¹H-NMR (CDCl₃): δ [ppm] |
|---|---|---|---|---|---|
| 23 | CH₃ | C(CH₃)₃ | H | CH₂CH(CH₃)₂ | 6.89(s 2H); 4.47(s 2H); 3.20(d 2H); 2.28 (s 3H); 2.14(s 6H); 1.75 8m 1H); 1.43(s 9H); 0.85(d 6H) |
| 24 | CH₃ | H | H | CH(CH₃)₂ | 57–59° C. |
| 25 | H | CH=CH(CH₃)₂ | H | CH(CH₃)₂ | 6.91(s 2H); 6.32(s 1H); 5.90(bs 1H); 5.13 (s 2H); 3.85(sp 1H); 2.30(s 3H); 2.21(s 3H); 2.10(s 6H); 1.97 (s 3H); 1.13(d 6H) |
| 26 | CH₃ | 2-pyridyl | H | CH₂CH₃ | 124–125° C. |
| 27 | CH₃ | 6-methyl-2-pyridyl | H | CH₂CH(CH₃)₂ | 7.70(AB 2H); 7.18(X 1H); 6.91(s 2H); 4.55 (s 2H); 3.21(d 2H); 2.61(s 3H); 2.37(s 3H); 2.28(s 3H); 2.16 (s 6H); 1.78(m 1H); 0.85(d 6H) |
| 28 | CH₃ | 6-methyl-2-pyridyl | H | CH(CH₃)₂ | 94–95° C. |
| 29 | CH₃ | 2,2-difluoro-1-methylcyclopropyl | H | CH₂C≡CH | 6.88(s 2H); 4.64(s 2H); 4.12(d 2H); 2.38 (t 1H); 2.25(s 3H); 2.12 (2s 3+3H); 2.03(s 3H); 1.92(m 1H); 1.50(s 3H); 1.42(m 1H) |
| 30 | CH₃ | 2,2-difluoro-1-methylcyclopropyl | H | CH₂CH(CH₃)₂ | 6.90(s 2H); 4.50(AB 2H); 3.22(d 2H); 2.26 (s 3H); 2.12(s 3H); 2.11(s 3H); 2.02(s 3H); 1.93(m 1H); 1.77 (m 1H); 1.51(s 3H); 1.43(m 1H); 0.85 (d 6H) |

TABLE 1-continued (I-a)

[Structure showing pyrone with R¹, R² substituents and trimethylphenyl group, with positions A and D]

| Ex. No. | A | D | R¹ | R² | Physical data: m.p. or ¹H-NMR (CDCl₃): δ [ppm] |
|---|---|---|---|---|---|
| 31 | CH₃ | [2,2-difluoro-1-methylcyclopropyl] | H | CH(CH₃)₂ | 6.88(s 2H); 4.52(AB 2H); 3.75(sp 1H); 2.26 (s 3H); 2.11(2s 3+3H); 2.01(s 3H); 1.92(m 1H); 1.50(s 3H); 1.41 (m 1H); 1.11(2d 3+3H) |
| 32 | CH₃ | [cyclopentyl] | H | CH₂CH₃ | 65–68° C. |
| 33 | CH₃ | [cyclopentyl] | H | CH₂C≡CH | 6.88(s 2H); 4.62(s 2H); 4.09(d 2H); 3.16 (m 1H); 2.40(t 1H); 2.25(s 3H); 2.13(s 6H); 2.02(s 3H); 1.8–1.95(m 6H); 1.6–1.7(m 2H) |
| 34 | CH₃ | [cyclopentyl] | H | CH(CH₃)₂ | 6.88(s 2H); 4.50(s 2H); 3.72(sp 1H); 3.15 (m 1H); 2.27(s 3H); 2.13(s 6H); 2.01(s 3H); 1.8–1.95(m 6H); 1.6–1.7(m 2H); 1.10(d 6H) |
| 35 | CH₃ | [cyclopentyl] | H | CH₂CH(CH₃)₂ | 6.88(s 2H); 4.47(s 2H); 3.20(d 2H); 3.18 (m 1H); 2.25(s 3H); 2.12(s 6H); 2.01(s 3H); 1.8–1.95(m 6H); 1.74(m 1H); 1.6–1.7(m 2H); 0.83(d 6H) |

Example 36

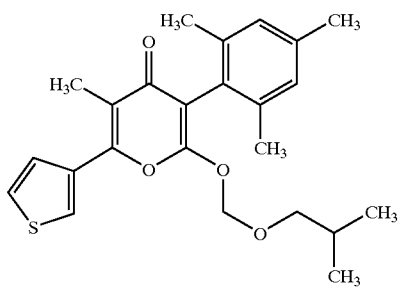

2-[(2-Methyl-1-propoxy)-methoxy]-5-methyl-6-(3-thienyl)-3-(2,4,6-trimethyl-phenyl)-4-pyrone melting at 102–104° C. was obtained in a similar manner to Example 1 from 4-hydroxy-5-methyl-6-(3-thienyl)-3-(2,4,6-trimethylphenyl)-2-pyrone and i-butoxychloromethane.

Examples 37–43

The compounds of the formula (I-b) which are listed in Table 2 below were obtained in a similar manner to Examples 1 and 2 and in accordance with the general details on preparation.

TABLE 2

(l-b)

[Structure: pyranone ring with substituents A, D, R²OCH₂O–, and phenyl bearing X, Y, Zₙ]

| Ex. No. | A | D | X | Y | Zₙ | R² | Physical data: m.p. or ¹H-NMR (CDCl₃): δ [ppm] |
|---|---|---|---|---|---|---|---|
| 37 | CH₃ | 2-pyridyl (methyl-substituted) | CH₃ | CH₃ | 6-OCH₃ | CH₂CH₃ | 116–118° C. |
| 38 | CH₃ | 2-pyridyl (methyl-substituted) | CH₃ | CH₃ | 5-CH₃ | CH₂C≡CH | 8.70(m 1H); 7.92(m 1H); 7.82(m 1H); 7.32(m 1H); 7.04(s 1H); 7.01(s 1H); 4.76 (AB 2H); 4.11(d 2H); 2.40(t 1H); 2.39(s 3H); 2.23(s 3H); 2.21 (s 3H); 2.19(s 3H); |
| 39 | CH₃ | 2-pyridyl (methyl-substituted) | CH₃ | CH₃ | 5-CH₃ | CH₂CH₃ | 8.70(m 1H); 7.92(m 1H); 7.82(m 1H); 7.33(m 1H); 7.03(s 1H); 7.01(s 1H); 4.62 (AB 2H); 3.55(q 2H); 2.40(s 3H); 2.22(s 3H); 2.21(s 3H); 2.19 (s 3H); 1.12(t 3H) |
| 40 | CH₃ | cyclopentylmethyl | CH₃ | CH₃ | 5-CH₃ | CH₂CH₃ | 6.98(s 1H); 6.92(s 1H); 4.54(AB 2H); 3.51(q 2H); 3.14(m 1H); 2.21(s 3H); 2.19 (s 3H); 2.15(s 3H); 2.01(s 3H); 1.80–1.95 (m 6H); 1.55–1.70(m 2H); 1.12(q 3H) |
| 41 | CH₃ | 2-pyridyl (methyl-substituted) | CH₃ | Br | 6-CH₃ | CH₂CH₃ | 132–134° C. |
| 42 | CH₃ | 2-pyridyl (methyl-substituted) | CH₃ | CH₃ | 5-CH₃ | CH₂—CH(CH₃)₂ | 8.70(m 1H); 7.92(m 1H); 7.82(m 1H); 7.33(m 1H); 7.03(s 1H); 7.01(s 1H); 4.62 (AB 2H); 3.23(d 2H); 2.40(s 3H); 2.24(s 3H); 2.22(s 3H); 2.20 (s 3H); 0.75(m 1H); 0.84(d 3H) |
| 43 | CH₃ | 4-fluorophenylmethyl | CH₃ | CH₃ | 6-OCH₃ | CH₂CH₃ | 101–103° C. |

Continuation of Table 1:

| Ex. No. | A | D | R¹ | R² | Physical data: m.p. or ¹H-NMR (CDCl₃): δ [ppm] |
|---|---|---|---|---|---|
| 44 | | —(CH₂)₄— | H | CH(CH₃)₂ | 6.85(s, 2H); 4.47(s, 2H); 3.73(sp, 1H); 1.10(d, 6H) |
| 45 | | —C(CH₃)₂OC(CH₃)₂— | H | CH₂CH₃ | 112–115° C. |
| 46 | | —C(CH₃)₂OC(CH₃)₂— | H | CH(CH₃)₂ | 94–96° C. |
| 47 | | —C(CH₃)₂OC(CH₃)₂— | H | CH₂CH(CH₃)₂ | 146–148° C. |
| 48 | | —C(CH₃)₂OC(CH₃)₂— | H | CH₂C≡CH | 102–104° C. |
| 49 | CH₃ | 3-methyl-1-butyl-1,2,4-triazol-5-yl (CH₃CH₂CH₂CH₂) | H | CH₂CH₃ | 8.00(s, 1H); 6.93(s, 2H); 4.60(s, 2H); 4.37(t, 2H); 3.57(q, 2H) |
| 50 | CH₃ | 3-methyl-1-ethyl-1,2,4-triazol-5-yl (CH₃CH₂) | H | CH(CH₃)₂ | 8.00(s, 1H); 6.93(s, 2H); 4.60(s, 2H); 4.45(q, 2H); 3.78(sp, 1H); 1.12(d, 6H) |

Continuation of Table 2:

| Ex. No. | A | D | X | Y | Z_n | R² | Physical data: m.p. or ¹H-NMR (CDCl₃): δ [ppm] |
|---|---|---|---|---|---|---|---|
| 51 | CH₃ | 2-pyridyl | CH₃ | F | H | CH₂CH(CH₃)₂ | 8.97(d, 1H); 7.93(d, 1H); 7.83(dt, 1H); 2.40(s, 3H); 2.28(s, 3H); 0.84(d, 6H) |
| 52 | CH₃ | 2-pyridyl | CH₃ | F | H | CH₂CH₃ | 4.63(AB, 2H); 2.40(s, 3H); 2.26(s, 3H); 1.13(t, 3H) |
| 53 | CH₃ | 4-fluorophenyl | CH₃ | Cl | H | CH₂CH₃ | 4.60(AB, 2H); 2.28(s, 3H); 2.13(s, 3H); 1.13(t, 3H) |
| 54 | CH₃ | 4-fluorophenyl | CH₃ | Cl | H | CH₂C≡CH | 4.73(AB, 2H); 4.60(d, 2H); 2.42(t, 1H); 2.27(s, 3H); 2.13(s, 3H) |
| 55 | CH₃ | 4-fluorophenyl | CH₃ | Cl | H | CH₂CH(CH₃)₂ | 89–91° C. |
| 56 | CH₃ | 4-fluorophenyl | CH₃ | Cl | H | CH(CH₃)₂ | 4.63(AB, 2H); 2.26(s, 3H); 2.13(s, 3H); 1.10(dd, 6H) |

-continued

Continuation of Table 2:

| Ex. No. | A | D | X | Y | $Z_n$ | $R^2$ | Physical data: m.p. or $^1$H-NMR (CDCl$_3$): δ [ppm] |
|---|---|---|---|---|---|---|---|
| 57 | CH$_3$ | 2-pyridyl | CH$_3$ | OCH$_3$ | H | CH$_2$CH(CH$_3$)$_2$ | 8.67(d, 1H); 7.90(d, 1H); 4.60(AB, 2H); 3.80(s, 3H); 2.40(s, 3H); 2.26(s, 3H); 0.85(d, 6H) |
| 58 | CH$_3$ | 2-pyridyl | CH$_3$ | OCH$_3$ | H | CH$_2$CH$_3$ | 8.66(d, 1H); 7.93(d, 1H); 4.60(AB, 2H); 3.83(s, 3H); 2.40(s, 3H); 2.27(s, 3H); 1.13(dd, 6H) |
| 59 | CH$_3$ | 4-F-phenyl | CH$_3$ | OCH$_3$ | H | CH$_2$CH(CH$_3$)$_2$ | 4.60(AB, 2H); 3.80(s, 3H); 2.26(s, 3H); 2.12(s, 3H); 0.85(d, 6H) |
| 60 | CH$_3$ | 4-F-phenyl | CH$_3$ | OCH$_3$ | H | CH$_2$CH$_3$ | 4.62(AB, 2H); 3.80(s, 3H); 2.27(s, 3H); 2.13(s, 3H); 1.17(t, 3H) |

Use Examples

Example A

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), while the leaves are still moist.

After the specified period of time, the destruction in % is determined. 100% means that all the beetle larvae have been killed; 0% means that none of the beetle larvae have been killed.

In this test, the compounds according to Preparation Examples 4, 5, 9, 26, 27, 28 and 31, for example, showed a degree of destruction of 100% after 7 days at an exemplary active compound concentration of 0.01%.

Example B

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with caterpillars of the diamond-back moth (Plutella maculipennis), while the leaves are still moist.

After the specified period of time, the destruction in % is determined. 100% means that all the caterpillars have been killed; 0% means that none of the caterpillars have been killed.

In this test, the compounds according to Preparation Examples 4, 5, 9, 10, 18, 27, 28, 31, 32 and 34, for example, showed a degree of destruction of 100% after 7 days at an exemplary active compound concentration of 0.1%.

Example C

Spodoptera Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with caterpillars of the owlet moth (Spodoptera frugiperda), while the leaves are still moist.

After the specified period of time, the destruction in % is determined. 100% means that all the caterpillars have been killed; 0% means that none of the caterpillars have been killed.

In this test, the compounds according to Preparation Examples 4, 5, 9, 32 and 34, for example, showed a degree of destruction of 100% after 7 days at an exemplary active compound concentration of 0.1%.

Example D

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (Oryzae sativa) are treated by being dipped into the preparation of the active compound of the desired concentration and are infested with larvae of the green rice leafhopper (Nephotettix cincticeps), while the seedlings are still moist.

After the specified period of time, the destruction in % is determined. 100% means that all the leafhoppers have been killed; 0% means that none of the leafhoppers have been killed.

In this test, the compounds according to Preparation Examples 1, 4, 7, 9, 11, 18, 21, 26, 27, 28, 29, 30, 31, 32 and 33, for example, showed a degree of destruction of 100% after 6 days at an exemplary active compound concentration of 0.1%.

Example E

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) which are highly infested by the peach aphid (Myzus persicae) are treated by being dipped into the preparation of the active compound of the desired concentration.

After the specified period of time, the destruction in % is determined. 100% means that all the aphids have been killed; 0% means that none of the aphids have been killed.

In this test, the compounds according to Preparation Examples 1, 9, 11, 26, 27, 31, 32 and 36, for example, showed a degree of destruction of 95 to 100% after 6 days at an exemplary active compound concentration of 0.1%.

Example F

Limit Concentration Test/Root-systemic Action

Test insect: Aphis fabae

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of no importance in practise, only the amount by weight of active compound per unit volume of soil, which is given in ppm (=mg/l), being decisive. The treated soil is transferred into pots and these are planted with beans (Vicia faba). The active compound can in this way be taken up from the soil by the roots of the plants and be transported into the leaves.

To demonstrate the root-systemic effect, the leaves only are infested with black bean aphids (Aphis fabae) after 7 days. After a further 2 days, the evaluation is made by counting or estimating the dead animals. The root-systemic action of the active compound is deduced from the destruction figures. It is 100% if all test animals have been killed and 0% if just as many test insects are still alive as in the case of the untreated control.

In this test, the compounds according to Preparation Examples 1, 10 and 11, for example, showed a degree of destruction of 100% at an examplary active compound concentration of 20 ppm.

Example G

Tetranychus Test (Resistance)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are highly infested by all development stages of the common spider mite (Tetranychus urticae) are treated by being dipped into the preparation of active compound of the desired concentration.

After the specified period of time, the destruction in % is determined. 100% means that all the spider mites have been killed 0% means that none of the spider mites have been killed.

In this test, the compounds according to Preparation Examples 9, 10, 11, 21 and 30, for example, gave a degree of destruction of 100% after 13 days at an exemplary active compound concentration of 0.01%.

Example H

Sphaerotheca Test (Cucumber)/Protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23 to 24° C. and at a relative atmospheric humidity of about 75%.

Evaluation is carried out 10 days after the inoculation.

In this test, the compounds according to Preparation Examples 1,2,4,7,8,9,10,11,17,18 and 21, for example, showed an activity of 100% in comparison with the untreated control at an exemplary active compound concentration of 100 ppm.

Example I

Venturia Test (Apple)/Protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet.

After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then. placed in a greenhouse at 20° C. and a relative atmospheric humidity of about 70%.

Evaluation is carried out 12 days after the inoculation.

In this test, the compounds according to Preparation Examples 4, 9 and 18, for example, showed an activity of 95–99% in comparison with the untreated control at an exemplary active compound concentration of 100 ppm.

Example J
Botrytis Test (Bean)/Protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, the compounds according to Preparation Examples 4, 9 and 18, for example, showed an activity of 94–99% in comparison with the untreated control at an exemplary active compound concentration of 500 ppm.

Example K
Pyricularia Test (Rice)/Protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. 4 days after the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation. In this test, the compounds according to Preparation Examples 4, 5, 8, 9, 10, 11 and 18, for example, showed an activity of 70–100% in comparison with the untreated control at an exemplary active compound concentration of 0.05%.

Example L
Test with Fly Larvae/Development-inhibiting Activity
Test animals: All larval stages of Lucilia cuprina (OP resistant) [Pupae and adults (without contact with the active compound)]
Solvent: 35 parts by weight of ethylene glycol monomethyl ether 35 parts by weight of nonylphenol polyglycol ether To produce a suitable formulation, 3 parts by weight of active compound are mixed with 7 parts of the solvent/emulsifier mixture specified above and the emulsion concentrate thus obtained is diluted with water to the desired concentration in each case.

For each concentration, 30 to 50 larvae are introduced into test tubes containing horse meat (1 cm$^3$), onto which 500 ml of the dilution under test are pipetted. The glass test tubes are placed in plastic beakers which have bottoms covered with sea sand and are kept in an air-conditioned room (26° C.±1.5° C., 70% relative humidity ±10%). The action is inspected after 24 hours and 48 hours (larvicidal action). After emigration of the larvae (approximately 72 h), the test tubes are removed and perforated plastic lids are placed on the beakers. After 1½ times the development period (emergence of the control flies), the emerged flies and the pupae/pupal cases are counted.

The criterion of activity used is the occurrence of death of the treated larvae after 48 h (larvicidal effect), or the inhibition of adult emergence from the pupae, or inhibition of pupal formation. The criterion used for the in-vitro activity of a substance is inhibition of fly development, or cessation of development prior to the adult stage. 100% larvicidal activity means that all larvae have died after 48 hours. 100% development inhibition activity means that no adult flies emerged.

In this test, the compounds according to Preparation Examples 1, 4, 9, 10, 11 and 18, for example, had an activity of 100% at an exemplary active compound concentration of 1000 ppm.

What is claimed is:
1. A compound of the formula (I):

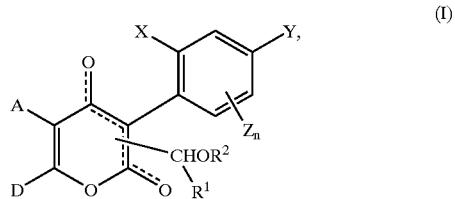

in which
X represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulfinyl, $C_1$–$C_6$-alkylsulfonyl; $C_1$–$C_6$-alkyl, $C_2$–$C_6$-alkenyl $C_1$–$C_6$-alkoxy or $C_2$–$C_6$-alkenyloxy, each of which is substituted by fluorine, chlorine or bromine; or phenyl, phenoxy, phenylthio, benzyloxy or benzylthio, each of which is optionally substituted by fluorine, chlorine, bromine, iodine, nitro, cyano or by $C_1$–$C_6$-alkyl or $C_1$–$C_6$-alkoxy, each of which is optionally substituted by fluorine, chlorine or bromine, Y represents hydrogen, fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy, $C_1$–$C_6$-alkylthio, $C_1$–$C_6$-alkylsulfinyl, $C_1$–$C_6$-alkylsulfonyl; or $C_1$–$C_6$-alkyl, $C_2$–$C_6$-alkenyl, $C_1$–$C_6$-alkoxy or $C_2$–$C_6$-alkenyloxy, each of which is substituted by fluorine, chlorine or bromine, Z represents fluorine, chlorine, bromine, iodine, nitro, cyano, $C_1$–$C_8$-alkyl, $C_2$–$C_6$-alkenyl, $C_1$–$C_6$-alkoxy, $C_2$–$C_6$-alkenyloxy or $C_1$–$C_6$-alkyl, $C_2$–$C_6$-alkenyl, $C_1$–$C_6$-alkoxy or $C_2$–$C_6$-alkenyloxy each of which is substituted by fluorine, chlorine or bromine, n represents one of the numbers 0, 1, 2 or 3, A represents hydrogen, fluorine, chlorine, bromine or iodine; a radical, selected from the group consisting of $C_1$–$C_{10}$-alkyl, $C_3$–$C_{10}$-cycloalkyl, $C_3$–$C_{10}$-alkenyl and $C_3$–$C_{10}$-alkinyl, which radical is optionally substituted by fluorine, chlorine, bromine or iodine; a radical selected from the group consisting of phenyl, naphthyl, and phenyl-$C_1$–$C_6$-alkyl, which radical is optionally substituted by fluorine, chlorine, bromine, iodine, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or cyano; or one of the groups —$COR^3$, —$CO_2R^3$, —CN, —$CONR^3R^4$, —$SO_2R^3$ or —$P(O)(OR^3)OR^4$, in which $R^3$ and $R^4$ independently of one another represent hydrogen; $C_1$–$C_{10}$-alkyl or $C_3$–$C_{10}$-alkenyl, each of which is optionally substituted by fluorine, chlorine, bromine or iodine; or a radical selected from the group consisting of phenyl, naphthyl, and phenyl-$C_1$–$C_6$-alkyl which radical is optionally substituted by fluorine, chlorine, bromine, iodine, nitro, $C_1$–$C_8$-alkyl, $C_1$–$C_8$-alkoxy, $C_1$–$C_8$-alkylthio, $C_1$–$C_8$-halogenoalkyl, $C_1C_8$-halogenoalkoxy or cyano, or D represents hydrogen; $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by fluorine, chlorine, bromine or iodine; cyano-, $C_1$–$C_8$-alkyloxycarbonyl- or $C_1$–$C_8$-alkylcarbonyloxy-substituted $C_1$–$C_{12}$-alkyl; $C_3$–$C_8$-cycloalkyl, which is optionally substituted by halogen, $C_1$–$C_4$-alkyl, $C_1$–$C_4$-alkoxy or $C_1$–$C_4$-halogenoalkyl and in which one or two not directly adjacent methylene groups are optionally replaced by oxygen and/or sulfur; or phenyl, phenyl-$C_1$–$C_6$-alkyl, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together represent a $C_2$–$C_7$-alkylene or $C_2$–$C_7$-alkenylene group, each of which is optionally substituted by $C_1$–$C_8$-alkyl, fluorine, chlorine, bromine or iodine and in which two carbon atoms are optionally joined by a $C_1$–$C_2$-alkylene group, $R^1$ represents hydrogen or $C_1$–$C_8$-alkyl, which is optionally substituted by fluorine, chlorine, bromine or iodine and $R^2$ represents $C_1$–$C_{10}$-alkyl, $C_3$–$C_{10}$-alkenyl or $C_3$–$C_{10}$alkinyl, each of which is optionally substituted by fluorine, chlorine, bromine or iodine.

2. The compound of the formula (I) according to claim 1, in which

X represents fluorine, chlorine, bromine, nitro, cyano, $C_1$–$C_6$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulfinyl, $C_1$–$C_4$-alkylsulfonyl; $C_1$–$C_4$-alkyl, $C_2$–$C_4$-alkenyl, $C_1$–$C_4$-alkoxy or $C_2$–$C_4$-alkenyloxy, each of which is substituted by fluorine or chlorine; or phenyl, phenoxy, phenylthio, benzyloxy or benzylthio, each of which is optionally substituted by fluorine, chlorine, bromine, nitro or cyano or by $C_1$–$C_4$-alkyl or $C_1$–$C_4$-alkoxy, each of which is optionally substituted by fluorine or chlorine, Y represents hydrogen, fluorine, chlorine, bromine, nitro, cyano, $C_1$–$C_6$-alkyl, $C_2$–$C_4$-alkenyl, $C_1$–$C_4$-alkoxy, $C_2$–$C_4$-alkenyloxy, $C_1$–$C_4$-alkylthio, $C_1$–$C_4$-alkylsulfinyl, $C_1$–$C_4$-alkylsulfonyl; or $C_1$–$C_4$-alkyl or $C_1$–$C_4$-alkoxy, each of which is substituted by fluorine or chlorine, Z represents fluorine, chlorine, bromine, nitro, cyano, $C_1$–$C_6$-alkyl, $C_1$–$C_4$-alkoxy, $C_2$–$C_4$-alkenyloxy; or $C_1$–$C_4$-alkyl or $C_1$–$C_4$-alkoxy, each of which is substituted by fluorine or chlorine, n represents one of the numbers 0, 1 or 2, A represents hydrogen, fluorine, chlorine or bromine; a radical selected from the group consisting of $C_1$–$C_8$-alkyl, $C_3$–$C_8$-cycloalkyl, $C_3$–$C_8$-alkenyl and $C_3$–$C_8$-alkinyl, which radical is optionally substituted by fluorine, chlorine or bromine; a radical selected from the group consisting of phenyl, naphthyl, phenyl-$C_1$–$C_4$-alkyl, which radical is optionally substituted by fluorine, chlorine, bromine, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or cyano; or one of the groups —$COR^3$, —$CO_2R^3$, —CN, —$CONR^3R^4$, —$SO_2R^3$ or —$P(O)(OR^3)OR^4$, in which $R^3$ and $R^4$ independently of one another represent hydrogen; $C_1$–$C_8$-alkyl or $C_3$–$C_8$-alkenyl, each of which is optionally substituted by fluorine, chlorine or bromine; or a radical selected from the group consisting of phenyl, phenyl-$C_1$–$C_4$-alkyl, which radical is optionally substituted by fluorine, chlorine, bromine, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or cyano, or D represents hydrogen; $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine; $C_1$–$C_8$-alkyl which is substituted by cyano, $C_1$–$C_6$-alkoxycarbonyl or $C_1$–$C_6$-alkylcarbonyloxy; $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl, and in which one or two non-directly adjacent methylene groups are optionally replaced by oxygen and/or sulfur; or phenyl, or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together represent a $C_2$–$C_6$-alkylene or $C_2$–$C_6$-alkenylene group, each of which is optionally substituted by $C_1$–$C_4$-alkyl, fluorine, chlorine or bromine, in which two carbon atoms are optionally connected by a $C_1$–$C_2$-alkylene group, $R^1$ represents hydrogen or $C_1$–$C_4$-alkyl which is optionally substituted by fluorine, chlorine or bromine and $R^2$ represents $C_1$–$C_8$-alkyl, $C_3$–$C_8$-alkenyl or $C_3$–$C_8$-alkinyl, each of which is optionally substituted by fluorine, chlorine or bromine.

3. The compound of the formula (I) according to claim 1, in which

X represents fluorine, chlorine, bromine, nitro, cyano, methyl, ethyl, n- or i-propyl, n-, s-, i- or t-butyl, vinyl, allyl, methallyl, methoxy, ethoxy, n- or i-propoxy, allyloxy, methallyloxy, trifluoromethyl, difluoromethoxy, trifluoromethoxy, trifluoroethoxy, methylthio, methylsulfinyl or methylsulfonyl, Y represents hydrogen, fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy, trifluoroethoxy, methylthio, methylsulfinyl or methylsulfonyl, Z represents fluorine, chlorine, bromine, nitro, cyano, methyl, ethyl, n- or i-propyl, n-, s-, i- or t-butyl, methoxy, ethoxy, n- or i-propoxy, allyloxy, methallyloxy, trifluoromethyl, difluoromethoxy, trifluoromethoxy or trifluoroethoxy, n represents either of the numbers 0 or 1, A represents hydrogen, fluorine, chlorine or bromine; a radical selected from the group consisting of $C_1$–$C_6$-alkyl, $C_3$–$C_6$-cycloalkyl, $C_3$–$C_6$-alkenyl and $C_3$–$C_6$-alkinyl, which radical is optionally substituted by fluorine or chlorine; phenyl, or benzyl, each of which is optionally substituted by fluorine, chlorine, bromine, methyl, ethyl, n-propyl, iso-propyl, methoxy, ethoxy, trifluoromethyl, trifluoro-methoxy, cyano or nitro; or one of the groups —$COR^3$, —$CO_2R^3$, —CN, —$CONR^3R^4$, —$SO_2R^3$ or —$P(O)(OR^3)OR^4$, in which $R^3$ and $R^4$ independently of one another represent hydrogen; $C_1$–$C_6$-alkyl or $C_3$–$C_6$-alkenyl, each of which is optionally substituted by fluorine or chlorine; or phenyl which is optionally substituted by fluorine, chlorine, bromine, nitro, $C_1$–$C_4$-alkyl, $C_1$–$C_4$-alkoxy, $C_1$–$C_4$-alkylthio, $C_1$–$C_4$-halogenoalkyl $C_1$–$C_4$-halogenoalkoxy or cyano, or D represents hydrogen; $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl or $C_1$–$C_4$-alkylthio-$C_2$–$C_4$-alkyl, each of which is optionally substituted by fluorine or chlorine; or $C_3$–$C_6$-cycloalkyl which is optionally substituted by fluorine, chlorine, methyl or ethyl and in which one or two non-directly adjacent methylene groups are optionally replaced by oxygen and/or sulfur; or phenyl, or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together represent one of the groups —$(CH_2)_3$, —$(CH_2)_4$, —$(CH_2)_5$—, —$CH_2$—$CH(CH_3)(CH_2)_2$— or

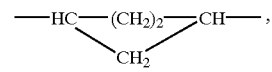

$R^1$ represents hydrogen; or methyl or ethyl, each of which is optionally substituted by fluorine or chlorine and $R^2$ represents methyl, ethyl, n- or i-propyl, n-, i-, s- or t-butyl, allyl, methallyl, butenyl, propargyl or butinyl, each of which is optionally substituted by fluorine or chlorine.

\* \* \* \* \*